(12) United States Patent
Galderisi

(10) Patent No.: US 8,906,426 B2
(45) Date of Patent: Dec. 9, 2014

(54) WATER-FREE, EMULSIFIER-FREE, AND PRESERVATIVE-FREE VEHICLE FOR ACTIVE INGREDIENTS

(71) Applicant: Alyson Galderisi, Cedar Grove, NJ (US)

(72) Inventor: Alyson Galderisi, Cedar Grove, NJ (US)

(73) Assignee: Alyson Galderisi, Cedar Grove, NJ (US)

( * ) Notice: Subject to any disclaimer, the term of this patent is extended or adjusted under 35 U.S.C. 154(b) by 0 days.

(21) Appl. No.: 13/679,844

(22) Filed: Nov. 16, 2012

(65) Prior Publication Data

US 2013/0122125 A1    May 16, 2013

Related U.S. Application Data

(60) Provisional application No. 61/560,602, filed on Nov. 16, 2011.

(51) Int. Cl.

| | | |
|---|---|---|
| A61K 36/00 | (2006.01) |
| A61K 36/76 | (2006.01) |
| A61K 36/886 | (2006.01) |
| A61K 8/97 | (2006.01) |
| A61K 8/34 | (2006.01) |
| A61K 8/98 | (2006.01) |
| A61K 8/81 | (2006.01) |

(52) U.S. Cl.
CPC .............. *A61K 8/97* (2013.01); *A61K 2800/31* (2013.01); *A61K 8/345* (2013.01); *A61K 8/982* (2013.01); *A61K 8/8182* (2013.01); *A61K 19/08* (2013.01)
USPC .......................................... 424/725; 424/744

(58) Field of Classification Search
None
See application file for complete search history.

(56) References Cited

U.S. PATENT DOCUMENTS

| | | | |
|---|---|---|---|
| 3,876,628 A | 4/1975 | Wright |
| 5,304,334 A | 4/1994 | Lahanas et al. |
| 5,552,135 A | 9/1996 | Cioca et al. |
| 5,610,199 A | 3/1997 | Cohen et al. |
| 5,698,206 A | 12/1997 | Becker et al. |
| 5,705,145 A | 1/1998 | Miklean et al. |
| 5,750,125 A | 5/1998 | Lahanas et al. |
| 5,780,517 A | 7/1998 | Cohen et al. |
| 6,036,965 A | 3/2000 | Gubernick et al. |
| 6,139,855 A | 10/2000 | Cioca et al. |
| 6,171,605 B1 | 1/2001 | Bevacqua et al. |
| 6,231,874 B1 | 5/2001 | Cioca et al. |
| 6,239,088 B1 | 5/2001 | George et al. |
| 6,451,328 B1 | 9/2002 | Ionita-Manzatu et al. |
| 6,592,882 B2 | 7/2003 | George et al. |
| 6,753,002 B2 | 6/2004 | George et al. |
| 6,777,450 B1 | 8/2004 | George et al. |
| 6,958,163 B2 | 10/2005 | Ionita-Manzatu et al. |
| 7,323,198 B2 | 1/2008 | Ionita-Manzatu et al. |
| 2003/0003117 A1 | 1/2003 | Marenick et al. |
| 2004/0180026 A1 | 9/2004 | Ha |
| 2005/0063932 A1 | 3/2005 | Dilallo et al. |
| 2007/0071704 A1 | 3/2007 | Brillouet et al. |
| 2008/0050398 A1 | 2/2008 | Bockmuehl et al. |
| 2008/0107679 A1 | 5/2008 | Dilallo et al. |
| 2011/0158922 A1 | 6/2011 | Dupont et al. |
| 2013/0338078 A1 | 12/2013 | Galderisi |

FOREIGN PATENT DOCUMENTS

WO    2004000242    12/2003

OTHER PUBLICATIONS

Packaging for "Zephyranthe" skincare product, International Edge, Inc., 2010.
Silvan, Rita, "Product Profile: La Mere," Elle Canada, 2010.
Lipotec, Snap-8 Solution C, an anti-aging peptide, Jul. 2008.
SK-influc, a skin-identical lipid concentrate for enhanced skin moisturization and protection, May 2003.
International Search Report, PCT/US12/65665, Mar. 14, 2013.

*Primary Examiner* — Qiuwen Mi

(74) *Attorney, Agent, or Firm* — Jeffrey L. Snow; Cooper & Dunham, LLP

(57) ABSTRACT

A vehicle for carrying active ingredients, wherein the vehicle is water-free, emulsifier-free, and preservative free. Preferably, the vehicle is used to carry a skin care formulation for treating skin conditions that provides noticeable results within two weeks or less.

8 Claims, No Drawings

WATER-FREE, EMULSIFIER-FREE, AND PRESERVATIVE-FREE VEHICLE FOR ACTIVE INGREDIENTS

CROSS-REFERENCE TO RELATED APPLICATION

This patent application claims the benefit of U.S. Provisional Patent Application Ser. No. 61/560,602, entitled "Topical Facial Cream to Improve Skin Appearance," filed Nov. 16, 2011, which application is incorporated in its entirety here by this reference.

BACKGROUND OF THE INVENTION

1. Technical Field

This invention relates to a vehicle for carrying active ingredients, preferably for topical treatment for skin conditions, wherein the vehicle is water-free, emulsifier-free, and preservative-free.

2. Background Art

There are many anti-aging creams claiming to work wonders on wrinkles and other skin blemishes associated with aging. However, a recent article published by Consumer Reports has indicated that these products had, at best, a small effect, and that these effects were not present in everyone after six weeks of treatment. Furthermore, any affect was short-lived. In the study, most of the test subjects indicated that they would buy what was revealed to be a simple moisturizer used as the control product. Therefore, current anti-aging creams are ineffective.

One factor contributing to the problem with anti-aging creams is that the creators are motivated by money from big corporations instead of the joy of accomplishment of making consumers feel beautiful. Furthermore, driven by profits, manufacturers of the top brands in the industry have separated the ingredients to address only one type of problem per cream in order to sell a larger variety of products. Big companies hold creative thinking back by trying to push more products.

Also, there are many different skin conditions that can be treated by many more different types of compounds. Trying to consolidate all the active ingredients for treatment of a variety of skin conditions can lead the creation of an irritant rather than a treatment. This is because in order to keep a formulation stable with many different active ingredients, a high quantity of emulsifier is required. High quantities of emulsifiers can be damaging or irritating to the skin.

Therefore, there is a need for a single formulation that is sufficiently stable and safe, and capable of addressing most aging skin problems, such as wrinkles, sun damage, uneven skin tone, tightness, elasticity, rosacea, spider veins, illumination, and the like. In general simply combining various skin care products together can lead to skin irritation for the user, or the combination simply will not mix well.

BRIEF SUMMARY OF INVENTION

The present invention is directed to a vehicle for carrying active ingredients wherein the vehicle is nearly completely water-free, preservative-free, and emulsifier-free. Preferably, the vehicle is used to carry an anti-aging formulation that is capable of treating a variety of skin conditions. The formulation contains numerous active ingredients for anti-aging with noticeable results within two weeks or less. In addition to being an all-in-one cream, it passes Repeat Insult Patch Testing (RIPT) test and Preservative Efficacy Testing (PET) without having any preservatives, which has never been done before. This is done by creating a formulation containing almost all active ingredients without the need for emulsifiers that hold the oil and water phases together, resulting in a very balanced pH.

DETAILED DESCRIPTION OF THE INVENTION

The detailed description set forth below is intended as a description of presently-preferred embodiments of the invention and is not intended to represent the only forms in which the present invention may be constructed or utilized. The description sets forth the functions and the sequence of steps for constructing and operating the invention. However, it is to be understood that the same or equivalent functions and sequences may be accomplished by different embodiments that are also intended to be encompassed within the spirit and scope of the invention.

The present invention is directed towards a water-free, emulsifier-free, and preservative-free vehicle for carrying active ingredients to treat, for example, skin conditions. Numerous active ingredients can be added to the vehicle for treating wrinkles, creating even skin tone, removing dark pigmentation, improving skin elasticity, repairing chemical insult, and treating other skin blemishes associated with aging and exposure to the environment. The present invention is also directed towards a method of preparing the vehicle with an anti-aging composition. The water-free, emulsifier-free, and preservative-free vehicle comprises aloe, pentylene glycol, willow bark extract, ammonium acryloyldimethyltaurate/VP copolymer, egg, and propolis. Each of these components may be present in amounts ranging from 0 percent to about 50% by weight of the total composition (% w/w). Preferably, the components are present in amounts ranging from 8% to about 35%.

In one embodiment, the components of the composition and their approximate percentage by weight are shown in Table 1 by their designation according to the international nomenclature of cosmetic ingredients (INCI). Trade names are provided as examples only and do not limit the scope of the invention of the present application. In the amounts disclosed, the components combine to make an anti-aging formulation that is nearly completely water-free, preservative-free, and emulsifier-free.

TABLE 1

| Group | INCI Name | Trade Name | Amt. % w/w | Preferred amt. % w/w | Function |
| --- | --- | --- | --- | --- | --- |
| 1 | Aloe Barbadensis Leaf Juice | Aloe Vera 1X Gel (Terry Labs) | 15-25 | 21 | Moisturizer and Anti-Irritant |
| 1 | Pentylene Glycol | Hydrolite-5 (Symrise) | 1-10 | 5 | Humectant, Moisturizer, |

TABLE 1-continued

| Group | INCI Name | Trade Name | Amt. % w/w | Preferred amt. % w/w | Function |
|---|---|---|---|---|---|
| 1 | Disodium EDTA | Dissolvine Na2 (Akzo) | <1 | 0.10 | and anti-bacterial Chelator |
| 1 | *Salix Nigra* (Willow) Bark Extract | Willow Bark Extract (Carrubba) | 10-20 | 15 | Active Anti-Wrinkle, Tone Normalizer, Beta Acid |
| 1 | PEG-8/SMDI Copolymer | Polyoprepolymer-15 (Barnet) | 0.5-5 | 2 | Anti-Systemic Delivery System |
| 1 | Propolis | | 0.5-10 | 2 | Anti-bacterial |
| 2 | Ammonium Acryloyldimethyltaurate/VP Copolymer | Aristoflex AVC (Clarient) | 0.5-5 | 1.25 | Gum |
| 3 | Caprylic/Capric Triglyceride | Liponate CG (Lipo) | 1-10 | 3 | Moisturizer |
| 3 | Cetearyl Alcohol, Ceteareth-20 | Lipowax-D (Lipo) | 1-10 | 2.50 | Structurizer |
| 3 | Tocopherol | Covi-OX T 50C (Cognis) | <1 | 0.25 | Vitamin E |
| 3 | Squalane | Squalane (Barnet) | 1-15 | 6 | Moisturizer (Most matches human sebum) |
| 3 | Bisabolol | Bisabolol (Lipo) | <1 | 0.02 | Anti-Irritant |
| 3 | Dipalmitoyl Hydroxyproline | Sepilift DPHP (Seppic) | 0.5-10 | 1 | Deep Wrinkle Remover |
| 3 | *Citrus Aurantium Dulcis* (Orange) Flower Wax | Deodorized Orange Wax (Koster-Keunen) | 0.5-10 | 2 | Natural Structurizer |
| 3 | *Butyrospermum Parkii* (Shea Butter) | Shea Butter (Sederma) | <1 | 0.75 | Unsaponifiable Deep Moisturizer |
| 3 | *Mangifera Indica* (Mango) Seed Butter | Mango Butter (Sederma) | <1 | 0.75 | Unsaponifiable Deep Moisturizer |
| 3 | Retinyl Palmitate | Vitamin-A (Essential Ingredients) | <1 | 0.10 | Anti-Wrinkle |
| 3 | Glycerin Soya (Soybean) Sterol | Net-Sterol-100 (Barnet) | <1 | 0.10 | Lipid |
| 3 | Dimethicone | Dow Corning 200/100 (Dow Corning) | 0.5-10 | 1.50 | Slip Agent |
| 3 | Tetrahexyldecyl Ascorbate | BV-OSC (Barnet) | 1-10 | 3 | Dark Spot Remover |
| 4 | Egg | Egg | 1-10 | 2 | Food Pyramid for Skin |
| 5 | *Pseudoalteromonas* Ferment Extract, Hydrolyzed Wheat Protein, Hydrolyzed Soy Protein, Tripeptide-10, Citrulline, Tripeptide-1, Lecithin, Xanthan Gum, Carbomer, Triethanolamine | Trylagen (Centerchem) | 1-10 | 3 | Anti-Wrinkle Complex |
| 5 | Glycerin, Butylene Glycol, Tetrapeptide-1 | Matrixyl 3000 (Croda) | 1-10 | 3 | Deep Wrinkle Remover |
| 5 | Acetyl Hexapeptide-8 | Argireline NP (Centerchem) | 1-10 | 5 | Laugh Line Wrinkles |
| 5 | Dipotassium Glycyrrhizinate | NET-DG (Barnet) | <1 | 0.25 | Anti-Irritant |
| 5 | Glycosaminoglycans | MDI (Unipex Innovation) | 1-10 | 5 | Rosacea and Spider Veins Remover |
| 5 | Glycosaminoglycans, Water, Glycerin, *Ahnfeltia Concinna* Extract | APT-GL (Centerchem) | 0.5-10 | 2 | Bio engineered algae for rebuilding damaged skin |
| 5 | Urea, Glucose, Guanidine, Tripeptide-1 | Kollaren PS 1-- (Atrium) | 1-10 | 3 | Anti-Wrinkle which encourages Collagen production |
| 5 | Acetyl Octapeptide-3 | Snap-8 (Centerchem) | 1-10 | 3 | Improvement for Laugh Lines |
| 5 | *Zea Mays* (Corn) Kernel Extract, Butylene Glycol, Xanthan Gum | Deliner (Unipex Innovation) | 1-10 | 3 | Anti-Wrinkle (for all wrinkles) Remover |

TABLE 1-continued

| Group | INCI Name | Trade Name | Amt. % w/w | Preferred amt. % w/w | Function |
|---|---|---|---|---|---|
| 5 | Polyamide-5 | Orgasol Caresse (Lipo) | 1-10 | 2 | Optical diminishes wrinkles under application (for temporary looks) |
| 5 | *Bambusa vulgaris* Extract, *Pisum sativum* (Pea) Extract, Glucosamine HCl | Derm SRC-PF | 1-10 | 3 | Part of Anti-Wrinkle Complex |
| 6 | Fragrance/Parfum | Fragrance Ungerer 839827 | <1 | 0.25 | Global Fragrance |

The components have been designated into one of six groups based on the preparation of the final formulation. The components and sequence of steps in formulating the composition is important in order to create a sufficiently stable and safe formulation that is generally water-free, preservative-free, and emulsifier-free. By generally or nearly water-free, preservative-free, or emulsifier-free it is to be understood that these components are not intentionally added to the composition; however, it is recognized that, for example, moisture from the air could enter into the formulation during processing in insignificant amounts. In addition, some components may inherently have some water, but the addition of this is an unintentional consequence of adding the other desired components. Nonetheless, the amount of water present can be less than 2%. In some embodiments it may be less than 1%, or even less than 0.5%. In general, the Group 1 non-oil components are combined into a batch and mixed, then heated to a desired temperature to kill any bacteria. Preferably, the components are mixed to uniformity while minimizing or preventing incorporation of air into the mixture. The Group 2 component is then added to the Group 1 component and mixed to uniformity. The mixing speed may be adjusted as the batch thickens.

In a separate second batch, the Group 3 oil or lipid components are combined and mixed, again, minimizing or preventing the introduction of any air during the mixing process. The second batch is heated to a desired temperature. Once the desired temperature is reached, the Group 4 component is added slowly. Proper agitation is maintained so as to avoid burning the Group 4 component in the oil from the Group 3 components.

While maintaining the target temperatures of each batch, the second batch is added to the first batch. Alternatively, the first batch can be added to the second batch. In either case, one batch is added to the other very slowly with maximum agitation, while minimizing or preventing the introduction of any air, to create a master batch emulsion. Top and bottom samples of the emulsion may be checked for quality. Preferably, emulsion quality is checked while the emulsification is maintained through mixing. Once the emulsion quality has passed a predetermined standard, the master batch is cooled to a desired temperature.

Once the desired temperature has been achieved, the Group 6 component can be added to the master batch and mixed, and further cooled to another predetermined temperature.

Once the predetermined temperature has been reached, the Group 5 components can be added one at a time to the master batch. After the addition of each Group 5 component, the master batch is mixed to uniformity before the next Group 5 component is added.

Once all of the components have been added and the emulsion is thoroughly mixed and cooled to another predetermined temperature. The top and bottom samples are checked again for emulsion quality. If emulsion quality passes a predetermined standard, then the formulation is complete. The anti-aging formulation can be topically applied.

The formulation can be applied as a cream, ointment, lotion, and the like. In some embodiments, the formulation may be incorporated into a patch and adhered to the skin. For example, in cream or lotion form, a dollop of approximately one-fifth the size of a dime can be applied to properly prepared skin and rubbed in every 12 hours. The cream can be applied twice a day, every day. Preferably, the cream is applied at night. It can even be applied with makeup on or makeup can be worn after application of the cream.

EXAMPLE 1

The following example is a preferred embodiment of the present formulation. In the preferred embodiment the anti-aging formulation is prepared in a "clean room" environment, without external air system blowers present. The container used to hold the components during the preparation process is sanitized and/or sterilized according to standard operating procedure and good manufacturing practice. For example, the container may be a stainless steel (3/16), jacketed, kettle equipped with a variable propeller, homogenizer and variable sweep agitation. A first batch of ingredients is made by combining and mixing the Group 1 components, then heating the batch to about 75 degrees Celsius (C) to about 85 degrees C., preferably about 76 degrees C. to about 80 degrees C., under adequate propeller agitation of approximately 700-800 RPM utilizing maximum tip speed. The components are mixed to uniformity with minimal introduction of air.

The Group 2, component is added slowly to the first batch and mixed to uniformity. The speed of the propeller agitation may be adjusted as the batch thickens.

A second batch is made in a second stainless steel kettle (3/16) properly sterilized and/or sanitized, by combining and mixing the Group 3 components together with adequate propeller agitation in such a way that the entire content in the second kettle are circulating without incorporation of air to create an oil phase. Then, the second batch is heated to about 75 degrees C. to about 85 degrees C., preferably about 80 degrees C. to about 82 degrees C. Once this target temperature has been reached, the egg from the Group 4 component is added slowly to the second batch while keeping the proper agitation to prevent the egg from burning while suspended in the oil.

At the targeted temperatures the second batch is slowly added to the first batch with maximum agitation and minimal to no incorporation of air to create an emulsion to form a master batch. While maintaining emulsification and mixing, the top and bottom samples of the emulsion are checked for emulsion quality by the quality assurance (QA) and/or quality control (QC) team. Once passed by the QA and/or QC team, the emulsion can be chilled with a refrigerant type cooling system, while switching to sweep as the batch thickens.

The master batch is then cooled quickly to about 42 degrees C. to about 45 degrees C. to prevent loss of aloe juice. The fragrance component of Group 6 can then be added to the master batch and cooled to about 35 degrees C. to about 37 degrees C., or even below 35 degrees C.

The Group 5 components can be added to the master batch one at a time, mixing to uniformity with each addition. Once all the components of group but have been added, the batch is cooled to approximately 25 degrees C. The top and bottom samples can be checked by the quality control and/or quality assurance team and released when approved.

Preferably, at any time an active ingredient is added to the formulation, the active ingredient is added at temperatures of about 35 degrees C. or less.

EXAMPLE 2

In one independent study conducted by the Essex Testing Clinic, Inc., the formulation of the present invention was used to determine the primary dermal irritation potential of the formulation when applied to the skin of human subjects for 48 hours under an occlusive patch. The study was based on approximately 53 subjects, 10 males and 43 females, ranging in age from 20 to 75 years. The subjects did not exhibit any physical or dermatologic condition that would have precluded application of the formulation or determination of potential effects of the formulation.

The formulation was applied in a sufficient amount (i.e. approximately 0.05 grams) to cover the patch (approximately half inch analytical paper disc). The patch containing the formulation was applied to the inner forearm of each subject for a period of 48 hours. At the end of 48 hours, the patch was removed and scored for dermal reactivity. A second reading was taken 48 hours later (i.e. 96 hours post-application). Dermal responses were scored according to the six-point scale shown in Table 2.

TABLE 2

| Score | Indication |
|---|---|
| 0 | No evidence of any effect |
| + | Barely perceptible (minimal, faint, uniform or spotty erythema) |
| 1 | Mild (pink, uniform erythema covering most of the contact site) |
| 2 | Moderate (pink-red erythema uniform in the entire contact site) |
| 3 | Marked (bright red erythema with/without petechiae or papules) |
| 4 | Severe (deep red erythema with/without vesiculation or weeping) |

All other observed dermal sequelae (e.g., edema, dryness, hypo- or hyperpigmentation) were appropriately recorded on the datasheet and described as mild, moderate or severe.

All subjects satisfactorily completed the test procedure. All subjects had a score of 0 on the six-point scale. In other words, there was no irritation observed at any time during the study on any subject after 48 hours of application and after an additional 48 hours from when the patch was removed (96 hours post-application).

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A generally water-free, preservative-free, and emulsifier-free composition for carrying active ingredients, comprising:
    a. aloe;
    b. pentylene glycol;
    c. willow bark extract;
    d. ammonium acryloyldimethyltaurate/VP copolymer; and
    e. egg, wherein the vehicle is generally water-free, preservative-free, and emulsifier-free.

2. The composition of claim 1, further comprising propolis.

3. The composition of claim 1, wherein the aloe, the pentylene glycol, the willow bark extract, the ammonium acryloyldimethyltaurate/VP copolymer, and the egg, are each present in an amount that is about 50% or less than the total composition by weight.

4. The composition of claim 3, wherein the aloe, the pentylene glycol, the willow bark extract, the ammonium acryloyldimethyltaurate/VP copolymer, and the egg, are each present in an amount ranging from about 8% to about 35% by weight.

5. The composition of claim 1, further comprising a compound selected from the group consisting of disodium EDTA and PEG-8/SMDI copolymer.

6. The composition of claim 1, further comprising a compound selected from the group consisting of capric triglyceride, cetearyl alcohol, ceteareth-20, tocopherol, squalane, bisabolol, dipalmitoyl hydroxyproline, citrus aurantium dulcis flower wax, butyrospermum parkii, mangifera indica seed butter, retinyl palmitate, glycerin soya sterol, dimethicone, and tetrahexyldecyl ascorbate.

7. The composition of claim 1, further comprising a compound selected from the group consisting of pseudoalteromonas ferment extract, hydrolyzed wheat protein, hydrolyzed soy protein, tripeptide-10, citrulline, tripeptide-1, lecithin, xanthan gum, carbomer, triethanolamine, glycerin, butylene glycol, tetrapeptide-1, acetyl hexapeptide-8, dipotassium glycyrrhizinate, glycosaminoglycans, glycerin, ahnfeltia concinna extract, urea, glucose, guanidine, acetyl octapeptide-3, zea mays kernel extract, polyamide-5, bambusa vulgaris extract, pisum sativum extract, and glucosamine HCl.

8. The composition of claim 1, further comprising a fragrance.

* * * * *